United States Patent
Price

(10) Patent No.: US 7,299,084 B1
(45) Date of Patent: Nov. 20, 2007

(54) PRECORDIAL OVERLAY AND DUAL BACKING ASSEMBLY

(75) Inventor: Michael A. Price, Cincinnati, OH (US)

(73) Assignee: CardioQuickSys, LLC, Sharonville, OH (US)

( * ) Notice: Subject to any disclaimer, the term of this patent is extended or adjusted under 35 U.S.C. 154(b) by 245 days.

(21) Appl. No.: 11/132,950

(22) Filed: May 20, 2005

(51) Int. Cl.
*A61B 5/0408* (2006.01)

(52) U.S. Cl. ...................... 600/372; 600/382

(58) Field of Classification Search ........ 607/149–153; 600/372, 393, 382–387, 390–392
See application file for complete search history.

(56) References Cited

U.S. PATENT DOCUMENTS

| | | |
|---|---|---|
| 5,995,861 A | 11/1999 | Price |
| 6,141,575 A | 10/2000 | Price |

*Primary Examiner*—George R. Evanisko
*Assistant Examiner*—Rex Holmes

(74) *Attorney, Agent, or Firm*—Charles R. Wilson

(57) ABSTRACT

A precordial overlay and dual backing assembly is expeditiously affixed together in a manner which allows it to be packaged in an unalterable form. When needed to obtain an ECG reading, the assembly is removed from the packaging and the precordial overlay swiftly separated from the dual backing. The dual backing is discarded. The precordial overlay is quickly and accurately positioned on a patient, The precordial overlay of the assembly comprises an elongated band having a first and a second generally rectangular-shaped sections joined together by an intermediate section. All three sections have at least one cut-out to receive an adhesive-backed electrode assembly. The dual backing of the assembly is similarly shaped and comprises a thin intermediate substrate with release agents on each side and a thin lower substrate with a release agent on a top side. The intermediate substrate further has a set of bent-back flaps, each flap positioned to receive an underside of one of the electrode assemblies. The flaps and the release agents of the dual backing allow the precordial overlay to be swiftly disassembled from the dual backing and used to obtain reliable test results in short order.

18 Claims, 4 Drawing Sheets

PRECORDIAL OVERLAY AND DUAL BACKING ASSEMBLY

FIELD OF THE INVENTION

This invention relates to a precordial overlay and dual backing assembly. For particularly, the invention relates to a precordial overlay and backing assembly which is expeditiously affixed together in an unalterable form for packaging purposes, yet swiftly disassembled for use. The precordial overlay is used to quickly and properly position electrodes on a patient as part of a electrocardiographic analysis.

BACKGROUND OF THE INVENTION

Electrocardiograms, commonly referred to as either ECGs or EKGs, are obtained from a patient as a diagnostic aid. They are often obtained as part of a routine physical exam conducted in a doctor's office. They are also obtained by emergency medical personnel on-site when responding to emergency runs initiated by a patient or concerned individual. A reliable reading is obtained if the personnel administering the test properly positions electrodes on the patient's chest. This can be challenging in an emergency situation given the circumstances under which the test is administered.

My U.S. Pat. Nos. 5,995,861 and 6,141,575 describe precordial overlays which address the need for a quick and accurate positioning of electrodes on a patient. The precordial overlay is an elongated band shaped for positioning on a patient's chest and further includes electrodes. The elongated band has cut-outs. A plurality of electrodes are specially configured as slidable electrode assemblies. They are mounted in the cut-outs. The elongated band allows for an approximate positioning of electrodes on the patient's chest and the manner of mounting allows a sliding of each assembly with its associated electrode to a precise chest location.

The patented precordial overlay has gained acceptance in emergency medical units and departments across the country. Greater efficiencies, though, are always desired in manufacturing products and in using products regardless of the industry. Such is the case with my precordial overlay. In accord with this general need, there has now been developed a precordial overlay which is more quickly manufactured in a form which can be packaged and transported. The resultant assembly is unalterable in the package, yet is swiftly disassembled on-site for use. Economic savings are achieved in manufacturing. Time savings are achieved by on-site emergency medical personnel. The savings are achieved without a sacrifice in quality or reliability of the overlay.

SUMMARY OF THE INVENTION

An assembly comprises a precordial overlay and a dual backing. It is expeditiously affixed together for packaging and transportation purposes in an unalterable form. Yet, it is readily removed from the package and swiftly disassembled for use of the precordial overlay on a patient to obtain reliable ECG test results. The precordial overlay comprises an elongated band with a set of cut-outs and electrode assemblies mounted in the cut-outs. The electrode assemblies have an adhesive on an underside which is needed to hold the electrode in place on a patient's chest during use. The dual backing of the assembly comprises thin intermediate and lower substrates similarly shaped to the elongated band. The intermediate substrate has release agent on both top and bottom sides and has a set of bent-back flaps positioned to receive the adhesive covered underside of each electrode assembly. The lower substrate has release agent on its top side. When assembled, the adhesive on the electrode assemblies contacts the bent-over flaps of the intermediate substrate and a portion of the lower substrate. The flap configuration and the release agents allow the precordial overlay to be swiftly separated in whole from the dual backing. The precordial overlay can then be used on a patient to obtain a quick and accurate positioning of the electrode assemblies.

DETAILED DESCRIPTION OF THE INVENTION

The precordial overlay and dual backing assembly of the invention is efficiently assembled for packaging and transport. The precordial overlay is readily separated from the dual backing. It is then used for quick and proper placement of electrode assemblies on a patient who is having an electrocardiographic test performed. The precordial overlay itself is primarily used by emergency medical personnel who often must quickly obtain an ECG. It can as well be used by medical personnel in a doctor's office setting as part of a routine physical examination.

Figure 1:
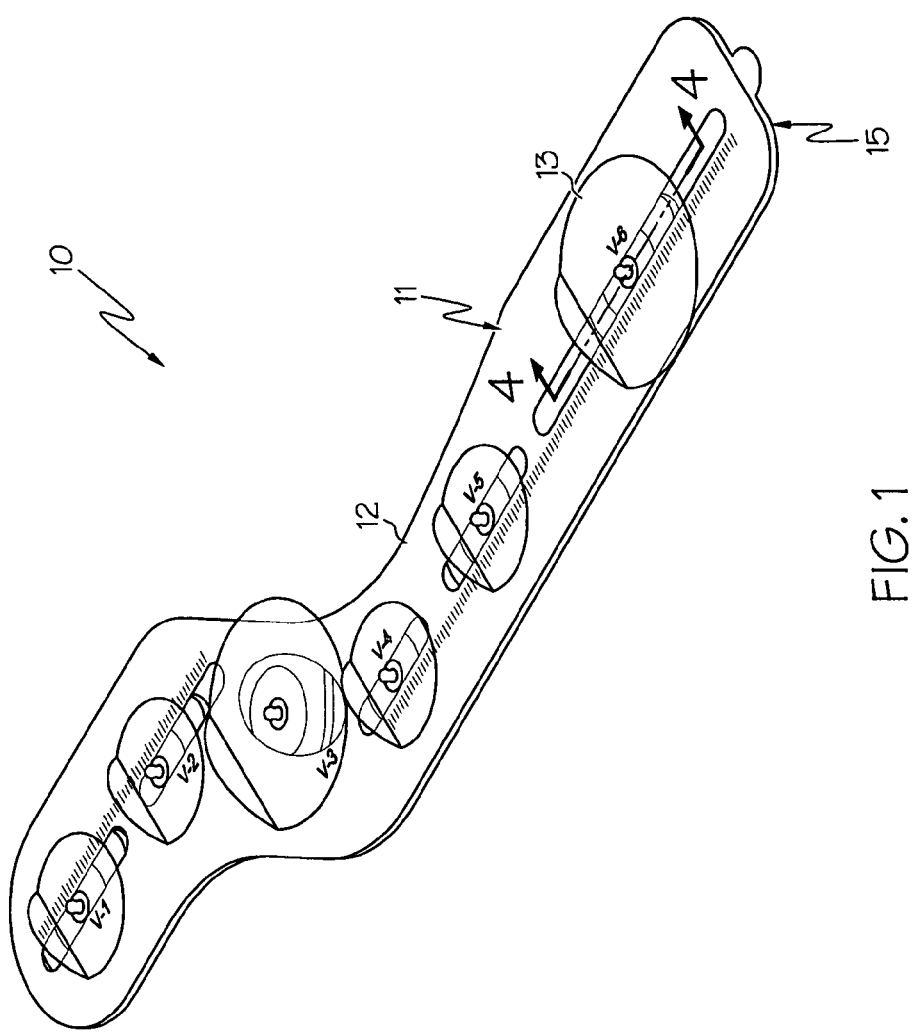
FIG. 1 is a perspective view of the precordial overlay and dual backing assembly of the invention.
Figure 2:
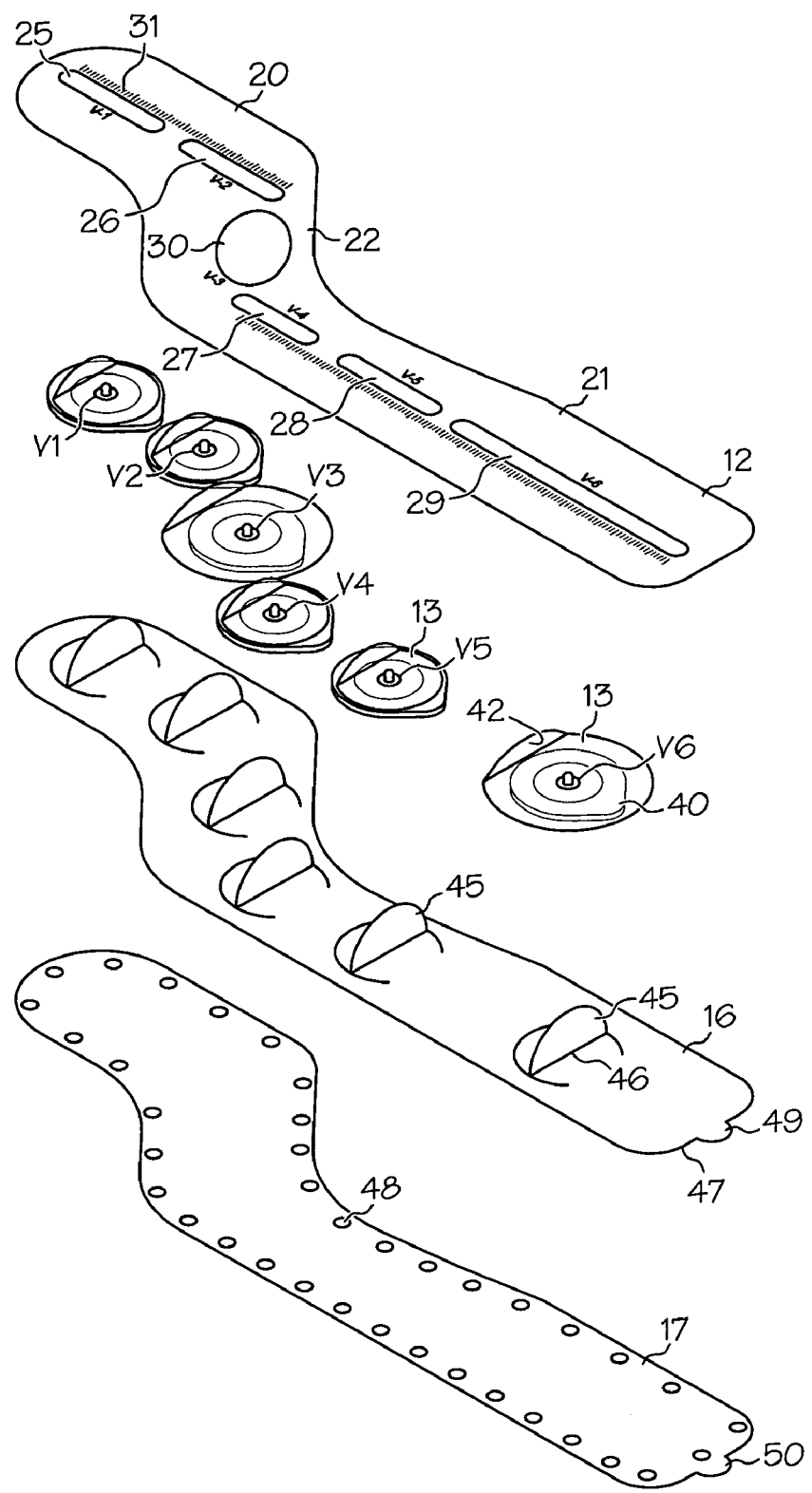
FIG. 2 is an exploded view of the assembly of FIG. 1 showing an elongated band and electrode assemblies of the precordial overlay as well as a thin intermediate substrate with a set of bent-over flaps and a thin lower substrate of the dual backing.

The precordial overlay and dual backing assembly 10 of the invention is depicted in FIGS. 1 and 2. The precordial overlay 11 component includes an elongated band 12 and a set of electrode assemblies 13 while the dual backing 15 component includes a thin intermediate substrate 16 and a thin lower substrate 17. Generally, the elongated band 12 of the precordial overlay is shaped to overlie a patient's chest. The electrode assemblies 13 are slidably mounted on the elongated band 12. The dual backing 15 is for packaging purposes with particular attention given to a need for a swift separation from the precordial overlay 11 without damage.

Figure 4:
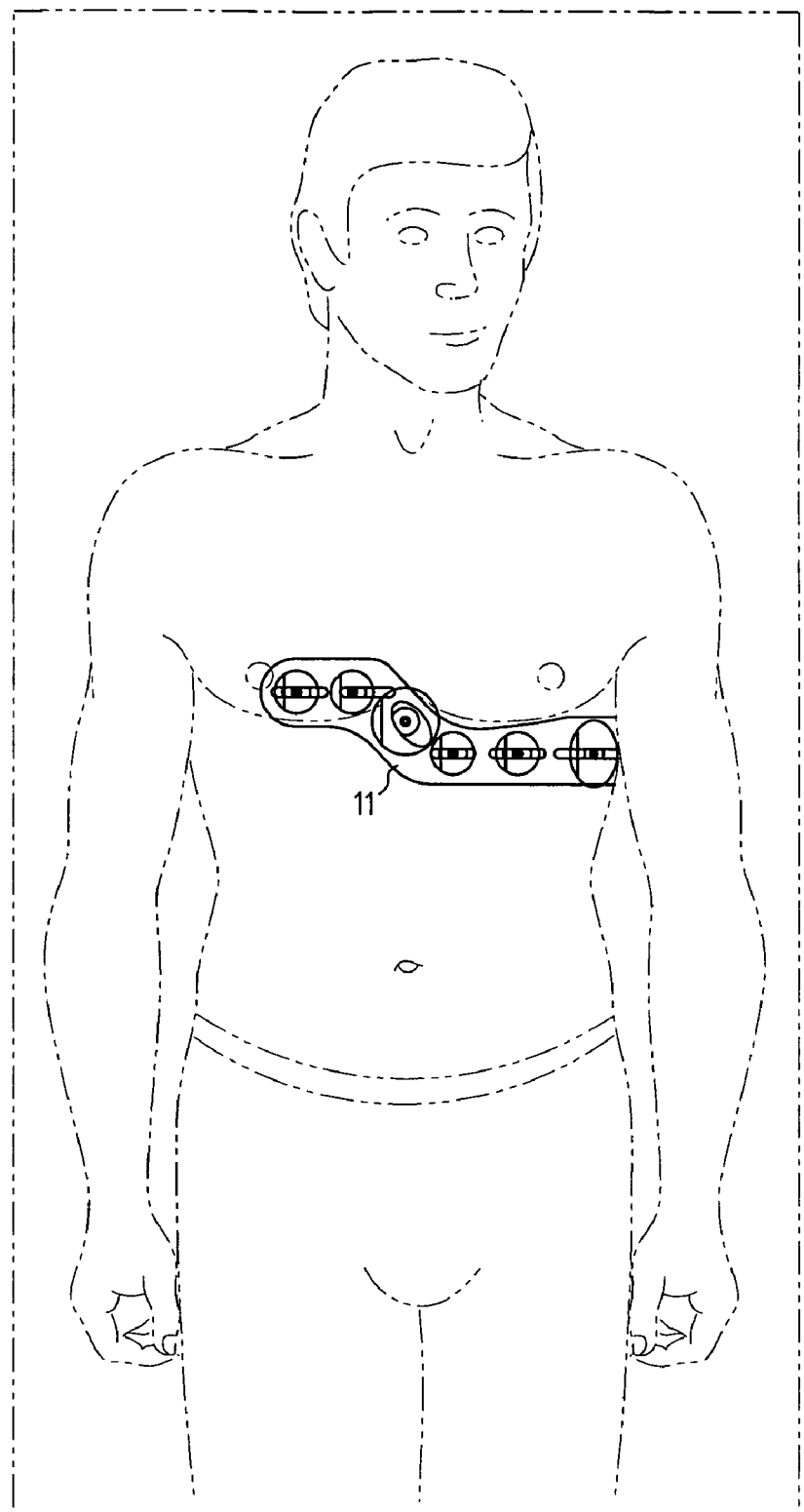
FIG. 4 is an environmental view showing the precordial overlay disassembled from its dual backing and positioned on a patient.

A highly preferred embodiment of the invention is depicted in FIG. 1. As apparent, five electrodes are slidably positioned in linear cut-outs while one electrode is slidably positioned in an oval cut-out. The precordial overlay's configuration allows emergency medical personnel to place the elongated band onto the patient's chest, as seen in FIG. 4, in the correct gross approximate location and then readily fine adjust the individual electrodes' precise chest location. A detailed description now follows of the components of the assembly 10 of the invention.

With particular reference to FIG. 2, the precordial overlay's elongated band 12 is thin and substantially flat. It is also sufficiently flexible to follow the contour of a patient's chest. It has a first generally rectangular-shaped section 20, a second generally rectangular-shaped section 21 and an intermediate section 22. The two generally rectangular-shaped sections are off-set from one another and extend in the same longitudinal direction. The intermediate section 22 connects the first and second generally rectangular-shaped sections 20 and 21. The shape of the band generally coincides with the area of the chest where electrodes must be positioned to obtain a reliable ECG.

The exact size of the elongated band is dependent on the size of the patient being tested, taking into consideration sex, age and body weight. Generally, because of the electrodes adjustability as described below, two sizes of the precordial overlay are adequate. A larger size is used for adults and a smaller size is used for children under the age of 14. Routine experimentation only is needed to determine the exact dimensions of the elongated band to meet its stated objectives.

The elongated band forming a part of the precordial overlay is made of a non-conductive material. A synthetic polymeric film is preferred because of its low material cost and capability of being given a desired shape by mass production techniques such as die-cutting. The precordial overlay of the invention is disposable primarily because the elongated band is capable of being produced at a reasonable cost. Polyethylene, polypropylene, polyvinylchloride, polyacrylate, polytetrafluoroethylene, nylon and polyester are examples of suitable polymeric films. A polyester film available as Mylar is particularly preferred.

Discreet cut-outs are provided in the body of the elongated band to accommodate the electrode assemblies. Six electrode assemblies 13 are slidably mounted in the elongated band 12. Each of the electrode assemblies includes an electrode identified by its medical nomenclature V1-V6.

Linear cut-outs 25 and 26 in the first generally rectangular-shaped section 20 of the elongated band 12 are configured to receive electrodes V1 and V2 and allow their assemblies to laterally slide for precise positioning purposes. The cut-outs 25 and 26 are approximately centered in the first section and run in the same lateral direction. One cut-out can be used in place of the two cut-outs, though is less preferred. Each cut-out 25 and 26 has a length to allow at least about 1.0 inch of electrode lateral movement. Preferably, the cut-outs are each about 1.5 inches to about 2.5 inches long and about 0.25 inches to about 0.5 inches wide.

Linear cut-outs 27, 28 and 29 in the second generally rectangular-shaped section 21 are configured to receive electrodes V4, V5 and V6 and their assemblies in a manner which allows them to slide within their respective cut-out until properly positioned for the particular patient. Cut-outs 27, 28, and 29 each has a length to allow at least about 1.0 inch of electrode lateral movement. Preferably, cut-out 27 is about 1.5 inches to about 2.0 inches long. Preferably, cut-out 28 is about 1.5 inches to about 2.5 inches long. Preferably, cut-out 29 is about 1.5 inches to about 5.5 inches long. All three cut-outs are about 0.25 inches to about 0.5 inches wide. Each cut-out allows only limited lateral movement of its associated electrode assembly. One cut-out extending the length of cut-outs 27-29 can be used instead of the three cut-outs 27-29. However, the three separate cut-outs are preferred to provide added precision in positioning of each of the electrodes V4, V5 and V6 and associated assembly.

The cut-out 30 in the intermediate section 22 is dimensioned to receive an electrode assembly and slidably hold it in position. The cut-out 30 is generally oval in shape with a major axis length of from about 1.5 inches to about 2.5 inches and a minor axis length of from about 1.0 inches to about 1.5 inches. This relatively small cut-out is sufficient to allow limited movement of the electrode V3 and its associated assembly in two directions.

Preferably, numeric scales 31 are printed onto the elongated band 12 of the precordial overlay. The scales are located just below or above the cut-outs 25 and 26 in the first generally rectangular-shaped section 20 and the cut-outs 27-29 in the second generally rectangular-shaped section 21. The numeric scales are used to record precise electrode placements in case a second reading is needed to verify an initial ECG.

Figure 3:
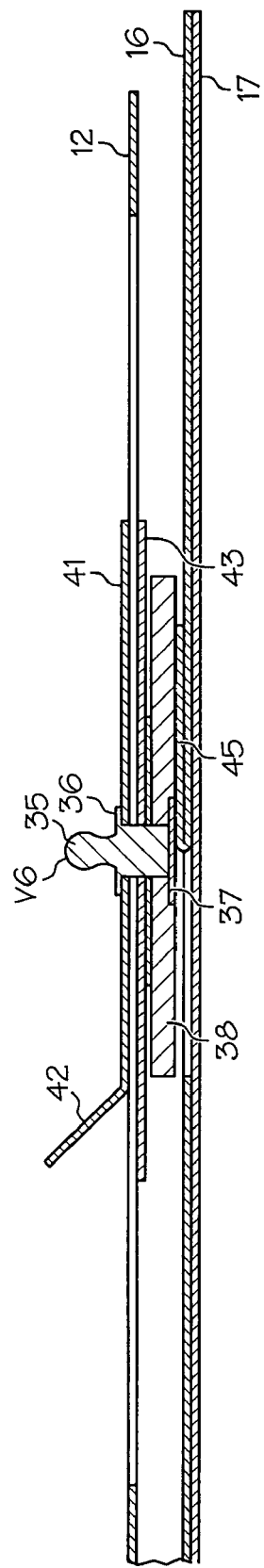
FIG. 3 is a side view in section taken along line 3-3 of FIG. 1 showing one of the electrode assemblies in detail.

The electrode assemblies 13 are specifically designed for use with the precordial overlay 11 of the invention. As best seen in FIG. 3, each assembly 13 is designed to remain in a cut-out, while allowing a sliding movement. The assembly 13 depicted includes the electrode V6 having a conductive metal post 35, a retention plate 36 and an underlying conductive foam disk 37. The vertically extending metal post 35 receives a cap head of a lead or wire (not illustrated) which is connected to the electrocardiograph. The height of the electrode V6 is sufficient to extend up through the cut-out 29 when mounted on the elongated band 12. The underlying foam disk 37 is used for comfort reasons in that it is the part of the electrode that contacts the patient's skin during the electrocardiographic test. The disk 37 is saturated with a conducting gel. It can as well be a simple conductive metal disk.

Still with reference to FIG. 3, the V6 electrode illustrated is mounted on a non-conductive pad 38 for ease of handling purposes. The non-conductive pad is made of a synthetic foam material and has a diameter greater than the width of the cut-out in which it is mounted. It has an adhesive on its underside for adhering to the patient. As best seen in FIG. 2, the non-conductive pad has a pull tab 40 extending from one side. The pull tab 40 has no adhesive on its underside. Its purpose is to provide a handle means for the medical personnel using the assembly to grasp and move an electrode assembly from below the elongated band during final patient positioning.

An upper clear plastic sheet 41 overlies the pad 38 and surrounds the metal post 35 of the electrode V6. Its diameter is greater than the width of the cut-out with which it is associated. The plastic sheet 41 is secured to the electrode, such that its peripheral areas are free or unattached. The plastic sheet's function is to provide a means to slidably hold its associated electrode V6 in the cut-out 29. Preferably, an edge segment 42 of the clear plastic sheet 41 is bent upwardly to serve as a handle to slide the assembly along the cut-out from above the elongated band if desired.

lower clear plastic sheet 43 adjacent the upper clear plastic sheet 41 while also overlying the non-conductive pad 38 is preferred for electrodes V3 and V6. The lower plastic sheet 43 is secured to the electrode in a manner similar to the upper plastic sheet 41. The two clear plastic sheets are about the same in shape and size. The two plastic sheets 41 and 43 in effect trap the electrode within the cut-out while allowing a sliding movement. It should be understood that without the lower plastic sheet 43, the non-conductive pad 38 can provide the same retention feature. However, the enhanced retention feature of the greater diameter and more rigid lower plastic sheet 43 is preferred at least for electrodes V3 and V6. It has been found the enhanced retention feature is beneficial to the V3 electrode because of its associated relatively larger width cut-out and beneficial to the V6 electrode because of its relatively larger length cut-out.

While not apparent in the drawings, it has also been found that for packaging purposes, adhesive tape is used to tape the electrode assembly for electrode V3 to the elongated band 12. It is ideally placed under the overlying plastic sheet to contact the top side of the non-conductive pad and the top side of the elongated band.

The dual backing 15, as seen in FIG. 2, comprises an intermediate substrate 16 and a lower substrate 17. Each of the substrates 16 and 17 has substantially the same size and shape as the elongated band 12 of the precordial overlay. All are thin. As evident in FIG. 1, the elongated band 12, the intermediate substrate 16 and the lower substrate 17 are configured substantially the same so that when formed into the assembly of the invention, they appear as three discreet layers, one on top of the other.

The intermediate substrate 16 has a release agent on its top side and its bottom side. A double sided silicone coating is preferred. Further, a set of bent backwardly flaps 45 are positioned along the length of the substrate such that each flap underlies one the cut-outs in the elongated band when the components of the invention are assembled together. The flaps 45 are created by die-cutting partial circles in the intermediate substrate and bending backwardly the cut portion at an approximate center line 46 thereof towards the free end 47 of the substrate's second generally rectangular-shaped section to create an upstanding flap. Preferably, the die-cut extends beyond the approximate center line for enhanced release. It should be apparent that the release agent on the underside of the intermediate substrate is now facing upwardly to receive the adhesive backing of an electrode assembly 13.

The thin lower substrate 17 has a release agent on its top side only. This is needed since the adhesive backing of each electrode assembly extends through the hole left by the bent backwardly flaps and contacts the lower substrate. Preferably, for manufacturing reasons as explained below, a series of vacuum holes 48 extend around its periphery.

Grasping tabs 49 and 50 on the intermediate substrate 16 and lower substrate 17, respectively are both located at the substrates' second generally rectangular-shaped sections free end. They serve as handles to separate the dual backing from the precordial overlay at the appropriate time.

In manufacture, the lower substrate is placed in a die of the same shape. A vacuum is drawn to hold it in place. The same vacuum force holds the intermediate substrate directly on top of the lower substrate. With the flaps of the intermediate layer bent backwardly, the electrode assemblies are placed onto the intermediate layer so as to fully cover the top side of the bent-back flap and to overlay the open space created by bending the flap backwardly. The elongated band can now be placed over the electrode assemblies and the upper plastic sheet of each electrode assembly manipulated to extend out through a cut-out and lie flat on the elongated band.

The time needed to manufacture the assembly of the invention is substantially reduced, thereby achieving a cost savings. The assembly is in form ready for packaging. The components of the assembly remain together in an unalterable form.

Medical emergency personnel first remove the precordial overlay and dual backing assembly from its packaging. The precordial overlay is separated for immediate use by holding the grasping tabs of the dual backing and pulling the elongated band in an opposed direction. The electrode assemblies, one by one, peel away from its respective underlying flap and the lower substrate directly thereunder. It is apparent the bent backwardly flaps facilitate release of the electrode assemblies from the dual backing. They do so in a manner whereby the integrity of the individual electrode assemblies is not compromised.

The freed precordial overlay is then placed on a patient using well known anatomical landmarks, e.g. a sternum notch. When properly positioned on the patient's chest, the cut-outs 25 and 26 in the first section 20 overlie the patient's fourth rib and the cut-outs 27-29 in the second section 21 overlie the patient's fifth rib. The cut-out 30 in the intermediate section 22 overlies an intercostal area between the fourth and fifth ribs or slightly overlies the fifth rib. It should be apparent that trained medical personnel can very quickly place the precordial overlay on a patient's chest so that the six cut-outs overlie the correct chest area. It is then just a matter of laterally moving the electrode assemblies 13 so that the electrodes V1, V2, V4, V5 and V6 are precisely located as known by the medical personnel. The electrode assembly with electrode V3 is moved laterally and longitudinally, though the precise positioning is readily accomplished. Another six electrodes used in conventional twelve lead electrocardiographic tests are not shown in FIG. 4. As well known, they are individually positioned at more remote body locations as currently done and are not a part of the invention. After use, the precordial overlay is discarded.

Having described the invention in its preferred embodiment, it should be clear that modifications can be made without departing from the spirit of the invention. It is not intended that the words used to describe the invention nor the drawings illustrating the same be limiting on the invention. It is intended that the invention only be limited by the scope of the appended claims.

I claim:

1. A precordial overlay and dual backing assembly expeditiously affixed together in an unalterable form for packaging and transporting purposes yet swiftly disassembled at time of use for placement of the precordial overlay on a patient's chest to facilitate a quick and accurate positioning of electrodes for an electrocardiographic test, said precordial overlay and dual backing assembly comprising:

(a) a precordial overlay having:

(1) an elongated band with a top side and a bottom side and having a first generally rectangular-shaped section, a second generally rectangular-shaped section, and an intermediate section connecting together the two generally rectangular-shaped sections so that they are off-set from one another and extend in the same direction, further wherein the first generally rectangular-shaped section has at least one cut-out configured to adjustably receive electrode assemblies, the second generally rectangular-shaped section has at least one cut-out configured to adjustably receive electrode assemblies and the intermediate section has a cut-out to adjustably receive an electrode assembly; and (2) a plurality of electrode assemblies operably associated with the elongated band, two of which are slidably mounted in the at least one cut-out of the first generally rectangular-shaped section to slide along a length thereof, three of which are slidably mounted in the at least one cut-out of the second generally rectangular-shaped section to slide along a length thereof and one of which is slidably mounted in the cut-out of the intermediate section to slide laterally and longitudinally therein, further each said electrode assembly comprising: (i) an electrode, (ii) an underlying non-conductive pad permanently secured to the electrode, said non-conductive pad having an underside with an adhesive thereon, (iii) an overlying plastic sheet having an approximately centered area and having circumjacent peripheral areas, further said overlying plastic sheet being permanently secured in said approximately centered area to the electrode and the circumjacent peripheral areas of said plastic sheet are positioned on the top side of the elongated band for sliding movement of the electrode assembly along the elongated band; and
(b) a dual backing having:
  (1) a thin intermediate substrate with a release agent on a top side and a release agent on a bottom side and having essentially the same shape as the elongated band of the precordial overlay and positioned thereunder, further said intermediate substrate having a series of upstanding flaps extending from the top side and spaced to underlie an electrode assembly of the precordial overlay and still further wherein each said flap has an approximate center line and is folded backwardly at said approximate center line to overlie the top side of the intermediate layer; and
  (2) a thin lower substrate with a release agent on a top side and having essentially the same shape as the elongated band of the precordial overlay and positioned under the intermediate substrate,
wherein the elongated band is positioned directly over both the intermediate substrate with said flaps all bent backwardly and the lower substrate so that they are substantially fully aligned and positioning each of the electrode assemblies in one of the cut-outs such that the overlying plastic sheet of the electrode assembly is resting on the top side of the elongated band and the non-conductive pad is on the bottom side of the elongated band and further a portion of the adhesive on the conductive pad is in contact with the bent backwardly flap of the intermediate substrate and another portion of the non-conductive pad is in contact with the top side of the lower substrate to affix together the precordial overlay and the dual backing, such that when the intermediate and lower substrates are grasped and the elongated band separated therefrom the electrode assemblies swiftly separate from the intermediate and the lower substrates and the precordial overlay with its operably associated electrode assemblies can be promptly positioned on the patient.

2. The precordial overlay and dual backing assembly of claim 1 wherein the first generally rectangular-shaped section of the elongated band has two cut-outs to each receive one electrode assembly and the second generally rectangular-shaped section of the elongated band has three cut-outs to each receive one electrode assembly.

3. The precordial overlay and dual backing assembly of claim 2 wherein the non-conductive pad of each electrode assembly has a tab extending from a periphery thereof.

4. The precordial overlay and dual backing assembly of claim 3 wherein each electrode assembly has a substantially vertically extending electrode for receiving an electrode lead wire, each said electrode having a diameter less than the width of a cut-out in which each said electrode is adjustably mounted so that the electrode can be grasped and manually moved in said cut-out while the overlying plastic sheet slides along the top side of said cut-out.

5. The precordial overlay of claim 4 wherein each of the cut-outs in the first generally rectangular-shaped section and in the second generally rectangular-shaped section of the elongated band has a length to allow at least about 1.0 inch of electrode movement.

6. The precordial overlay and dual backing assembly of claim 5 wherein the plurality of electrode assemblies includes an electrode V1, an electrode V2, an electrode V3, an electrode V4, an electrode V5 and an electrode V6 and further wherein (i) a first cut-out in the first generally rectangular section for electrode V1 is about 1.5 inches to about 2.5 inches long and about 0.25 inches to about 0.5 inches wide, (ii) a second cut-out in the first generally rectangular section for electrode V2 is about 1.5 inches to about 2.5 inches long and about 0.25 inches to about 0.5 inches wide, (iii) the cut-out in the intermediate section for electrode V3 has an oval shape with a major axis of about 1.0 inches to about 2.5 inches and a minor axis of from about 1.0 inches to about 1.5 inches, (iv) a first cut-out in the second generally rectangular section for electrode V4 is about 1.5 inches to about 2.0 inches long and about 0.25 inches to about 0.5 inches wide, (v) a second cut-out in the second generally rectangular section for electrode V5 is about 1.5 inches to about 2.5 inches long and about 0.25 inches to about 0.5 inches wide, and (vi) a third cut-out in the second generally rectangular section for electrode V6 is about 1.5 inches to about 5.5 inches long and about 0.25 inches to about 0.5 inches wide.

7. The precordial overlay and dual backing assembly of claim 1 further wherein each electrode assembly further has an underlying plastic sheet having an approximately centered area and having circumjacent peripheral areas with said underlying plastic sheet being permanently secured in said approximate center area to the electrode below the overlying plastic sheet and over the non-conductive pad and the circumjacent peripheral areas of said underlying plastic sheet are positioned on the bottom side of the elongated band for retaining the electrode assembly in the cut-out.

8. The precordial overlay and dual backing assembly of claim 1 wherein the elongated band of the precordial overlay and the intermediate substrate and the lower substrate of the dual backing all have substantially the same shape and size and are in alignment with one another.

9. The precordial overlay and dual backing assembly of claim 8 wherein the intermediate substrate and the lower substrate of the dual backing each has an aligned grasping tab extending from one end thereof for collectively holding as an aid in separating the dual backing from the precordial overlay.

10. The precordial overlay and dual backing assembly of claim 8 wherein the overlying plastic sheet of each electrode assembly has an edge segment bent upwardly for grasping as an aid in sliding the electrode assembly within its cut-out along the elongated band.

11. A precordial overlay and dual backing assembly expeditiously affixed together in an unalterable form for packaging and transporting purposes yet swiftly disassembled at time of use for placement of the precordial overlay on a patient's chest to facilitate a quick and accurate positioning of electrodes for an electrocardiographic test, said precordial overlay and dual backing assembly comprising:
(a) a precordial overlay having:
  (1) an elongated band with a top side and a bottom side and having a first generally rectangular-shaped section, a second generally rectangular-shaped section, and an intermediate section connecting together the two generally rectangular-shaped sections so that they are off-set from one another and extend in the same direction, further wherein the first generally rectangular-shaped section has two cut-outs configured to each adjustably receive an electrode assembly, the second generally rectangular-shaped section has three cut-outs configured to each adjustably receive an electrode assembly and the intermediate section has a cut-out to adjustably receive an electrode assembly; and (2) a set of six electrode assemblies operably associated with the elongated band, two of which are slidably mounted in the cut-outs of the first generally rectangular-shaped section to slide along a length thereof, three of which are slidably mounted in the cut-outs of the second generally rectangular-shaped section to slide along a length thereof and one of which is slidably mounted in the cut-out of the intermediate section to slide laterally and longitudinally therein, further each said electrode assembly comprising: (i) an electrode, (ii) an underlying non-conductive pad permanently secured to the electrode, said non-conductive pad having a pull tab for laterally moving the electrode assembly and having an underside with an adhesive thereon, (iii) an overlying plastic sheet having an approximately centered area and having circumjacent peripheral areas, further said overlying plastic sheet being permanently secured in said approximately centered area to the electrode and the circumjacent peripheral areas of said plastic sheet having an edge segment bent upwardly for grasping, said overlying plastic sheet positioned on the top side of the elongated band for sliding movement of the electrode assembly along the elongated band; and (b) a dual backing having:

(1) a thin intermediate substrate with a release agent on a top side and a release agent on a bottom side and having essentially the same shape as the elongated band of the precordial overlay and positioned thereunder, further said intermediate substrate having six upstanding flaps extending from the top side and spaced to underlie an electrode assembly of the precordial overlay and still further wherein each said flap has an approximate center line and is folded backwardly at said approximate center line towards a free end of the second generally rectangular-shaped section of the substrate to overlie the top side of the intermediate layer; and (2) a thin lower substrate with a release agent on a top side and having essentially the same shape as the elongated band of the precordial overlay and positioned under the intermediate substrate, wherein the elongated band is positioned directly over both the intermediate substrate with said flaps bent backwardly and the lower substrate so that they are substantially fully aligned and each of the electrode assemblies is positioned in one of the cut-outs such that the overlying plastic sheet of the electrode assembly is resting on the top side of the elongated band and the non-conductive pad is on the bottom side of the elongated band and further a portion of the adhesive on the conductive pad is in contact with the bent backwardly flap of the intermediate substrate and another portion of the non-conductive pad is in contact with the top side of the lower substrates to affix together the precordial overlay and the dual backing, such that when the intermediate and lower substrates are grasped and the elongated band separated therefrom the electrode assemblies swiftly separate from the intermediate and the lower substrate and the precordial overlay with its operably associated electrode assemblies can be quickly positioned on the patient.

12. The precordial overlay and dual backing assembly of claim 11 wherein each of the cut-outs in the first generally rectangular-shaped section and in the second generally rectangular-shaped section of the elongated band has a length to allow at least about 1.0 inch of electrode movement and has a width of about 0.25 inches to about 0.5 inches.

13. The precordial overlay and dual backing assembly of claim 12 further wherein each electrode assembly positioned in a cut-out of the elongated band has an underlying plastic sheet with an approximately centered area and circumjacent peripheral edges with said underlying plastic sheet being permanently secured in said approximate center area to the electrode below the overlying plastic sheet and over the non-conductive pad and circumjacent peripheral areas of said underlying plastic sheet are positioned on the bottom side of the elongated band for retaining the electrode assembly in the cut-out.

14. The precordial overlay and dual backing assembly of claim 11 wherein the elongated band of the precordial overlay and the intermediate substrate and the lower substrate of the dual backing all have substantially the same shape and size and are in alignment with one another.

15. The precordial overlay and dual backing assembly of claim 14 wherein the intermediate substrate and the lower substrate of the dual backing each has an aligned grasping tab extending from one end thereof for collectively holding as an aid in separating the dual backing from the precordial overlay.

16. A precordial overlay and dual backing assembly comprising:

(a) a precordial overlay having:

(1) an elongated band with a top side and a bottom side and having a first generally rectangular-shaped section, a second generally rectangular-shaped section, and an intermediate section connecting together the two generally rectangular-shaped sections so that they are off-set from one another and extend in the same direction, further wherein the first generally rectangular-shaped section has two cut-outs configured to each adjustably receive an electrode assembly, the second generally rectangular-shaped section has three cut-outs configured to each adjustably receive an electrode assembly and the intermediate section has a cut-out to adjustably receive an electrode assembly; and (2) a set of six electrode assemblies operably associated with the elongated band, two of the assemblies having electrodes V1 and V2 slidably mounted in the cut-outs of the first generally rectangular-shaped section, three of the assemblies having electrodes V4, V5, and V6 slidably mounted in the cut-outs of the second generally rectangular-shaped section and one of the assemblies having electrode V3 slidably mounted in the cut-out of the intermediate section, further each electrode assembly having electrodes V1, V2, V4, and V5 comprising: (i) an electrode, (ii) an underlying non-conductive pad permanently secured to the electrode, said non-conductive pad having an underside and a pull tab and further having an adhesive on said underside, (iii) an overlying plastic sheet having an approximately centered area and having circumjacent peripheral areas with an edge segment opposed the pull tab of the non-conductive pad bent upwardly for grasping as an aid in sliding the electrode assembly, further said overlying plastic sheet being permanently secured in its approximately centered area to the electrode and positioned on the top side of the elongated band for sliding movement of the electrode assembly therealong, each electrode assembly having electrodes V3 and V6 comprising: (i) an electrode, (ii) an underlying non-conductive pad permanently secured to the electrode, said non-conductive pad having an underside and a pull tab and further having an adhesive on said underside, (iii) an overlying plastic sheet having an approximately centered area and having circumjacent peripheral areas with an edge segment opposed the pull tab of the non-conductive pad bent upwardly for grasping as an aid in sliding the electrode assembly, further said, overlying plastic sheet being permanently secured in its approximately centered area to the electrode and positioned on the top side of the elongated band for sliding movement of the electrode assembly therealong, and (iv) an underlying plastic sheet having an approximately centered area and having circumjacent peripheral areas wherein the underlying plastic sheet is permanently secured in said approximately centered area to the electrode and the circumjacent peripheral areas of said plastic sheet are positioned on the bottom side of the elongated band for sliding movement of the electrode assembly therealong; and (b) a dual backing operably associated with the precordial overlay and positioned directly thereunder, said dual backing having:

(1) a thin intermediate substrate with a first generally rectangular-shaped section, a second generally rectangular-shaped section and an intermediate section connecting together the two generally rectangular-shaped sections, said intermediate substrate having a release agent on a top side and a release agent on a bottom side and having essentially the same shape as the elongated band of the precordial overlay and positioned thereunder, further said intermediate substrate having a grasping tab on a free end of the second generally rectangular-shaped section, and having six upstanding flaps extending from the top side and spaced to underlie an electrode assembly of the precordial overlay and still further wherein each said flap has an approximate center line and is folded backwardly at said approximate center line towards the free end of the second generally rectangular-shaped section of the substrate to overlie the top side of the intermediate layer; and (2) a thin lower substrate with a first generally rectangular-shaped section, a second generally rectangular-shaped section and an intermediate section connecting together the two generally rectangular-shaped sections, said lower substrate having a release agent on a top side and having essentially the same shape as the elongated band of the precordial overlay and positioned under the intermediate substrate, wherein the elongated band is positioned directly over both the intermediate substrate with the flaps folded backwardly and the lower substrate so that they are substantially fully aligned and positioning each of the electrode assemblies in one of the cut-outs such that the overlying plastic sheet of the electrode assembly is resting on the top side of the elongated band and the non-conductive pad is on the bottom side of the elongated band and further a portion of the adhesive on the conductive pad is in contact with the bent backwardly flap of the intermediate substrate and another portion of the non-conductive pad is in contact with the top side of the lower substrate to affix together the precordial overlay and the dual backing.

17. The precordial overlay and dual backing assembly of claim 16 wherein the elongated band of the precordial overlay and the intermediate substrate and the lower substrate of the dual backing all have substantially the same shape and size and are in alignment with one another.

18. The precordial overlay and dual backing assembly of claim 17 wherein the intermediate substrate and the lower substrate of the dual backing each has an aligned grasping tab extending from one end thereof for collectively holding as an aid in separating the dual backing from the precordial overlay.

* * * * *